United States Patent [19]

Hartlage

[11] 4,066,652

[45] Jan. 3, 1978

[54] SUBSTITUTED 8-HYDROXYQUINOLINES AND PROCESS FOR THE PREPARATION THEREOF

[75] Inventor: James A. Hartlage, Worthington, Ohio

[73] Assignee: Ashland Oil, Inc., Ashland, Ky.

[21] Appl. No.: 397,120

[22] Filed: Sept. 12, 1973

[51] Int. Cl.$^2$ ............................................ C07D 215/26
[52] U.S. Cl. ................................. 260/289 XA; 75/117
[58] Field of Search ........ 260/289 OX, 289 R, 289 XA

[56] References Cited

U.S. PATENT DOCUMENTS

| | | | |
|---|---|---|---|
| 3,536,717 | 10/1970 | Arrigo | 260/289 |
| 3,637,711 | 3/1968 | Buddle et al. | 260/289 R |
| 3,682,935 | 8/1972 | Law | 260/289 O X |

*Primary Examiner*—Donald G. Daus
*Assistant Examiner*—Mary Vaughn

[57] ABSTRACT

A class of hydrocarbyl substituted 8-hydroxyquinolines wherein the indicated substituent arises through the indirect alkylation of said quinolinol with a hindered aldehyde. These alkylates are useful metal collectors in hydrometallurgical extraction processes designed for the recovery of metal values from dilute aqueous solutions thereof.

4 Claims, No Drawings

SUBSTITUTED 8-HYDROXYQUINOLINES AND PROCESS FOR THE PREPARATION THEREOF

BACKGROUND OF THE INVENTION

1. Field Of The Invention

This invention relates to 8-hydroxyquinoline substituted with an alpha-alkenyl group on the non-hetero ring and to a process for the preparation of such derivatives.

2. Description Of The Prior Art

The compound 8-hydroxyquinoline is well known for its ability to coordinate with ions of a variety of transition metals through covalent bonding to form a relatively stable 5-membered ring which complexes are commonly referred to as metal chelates. This complexing technique has been used extensively heretofore in chemical analytical procedures. Recently, however, the ability of the 8-hydroxy quinoline configuration to form chelates with the transition metals has been utilized in hydrometallurgical extraction processes applicable for the recovery of such metal values from aqueous solutions thereof. These extraction processes comprise basically a two step operation. In the first step an impure aqueous phase containing the desired metal values in ionic form is intimately contacted with a water-immiscible organic solution of the metal collector to facilitate an interfacial relationship of the phases whereby the metal ions are readily and preferentially extracted into the organic phase in the form of a chelate. The second step, which is referred to as stripping, serves to regenerate the extracted metal values in ionic form and to effect the transfer thereof to an aqueous phase thus resulting in a pure and relatively concentrated solution of the desired metal from whence it can then be readily recovered such as by an electrolytic process.

Unfortunately, 8-hydroxyquinoline itself cannot be effectively used in the aforedescribed extraction processes because it is not sufficiently soluble in the hydrocarbon solvents employed to provide the organic phase and whereas it is too soluble in the acidic aqueous stripping phases. The deficiencies of 8-hydroxyquinoline in this regard can be overcome, however, by providing a bulky hydrocarbyl substituent thereon which, if properly chosen as to carbon atom content, will markedly enhance its oil-solubility characteristics; and at the same time reduce its solubility even in strong acidic aqueous mediums to essentially a nil value. It is also known that the molecular configuration of such a substituent is important from the standpoint of increasing the loading capabilities of the base compound.

A class of 8-hydroxyquinolines modified in the foregoing manner is exemplified in U.S. Pat. No. 3,637,711. These substituted 8-hydroxyquinolines are characterized in having a higher B-alkenyl group in the No. 7 position. The foregoing compounds have proven to be excellent collectors and can be effectively used in all types of metal extraction processes including those which require a pH range as low as 1-2. The only disadvantage of these prior art extractants is that their method of preparation calls for the use of a higher allylic chloride which is a difficult and thus a relatively expensive reagent to manufacture. Accordingly, the foremost objective of the present invention is to provide similarly functional 8-hydroxyquinoline derivatives as those of the aforementioned patent but which are substantially more economical to synthesize.

SUMMARY OF THE INVENTION

In accordance with this invention a class of alpha alkenyl substituted 8-quinolinols are provided corresponding to the following structural formula:

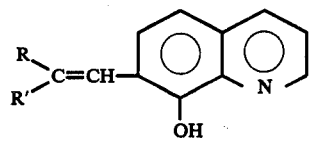

wherein R and R' represent alkyl groups having a sum total of from 6 to 18 carbon atoms.

In a further aspect, a process is provided for preparing the aforesaid compounds which comprises reacting 8-quinolinol with a branched secondary aldehyde having the formula:

wherein R and R' have the above-mentioned meanings. The foregoing process is carried out at an elevated temperature and under conditions facilitating the removal of water of dehydration ensuing upon, or concominantly generated in effecting the condensation of the aldehyde and the quinolinol.

DESCRIPTION OF THE PREFERRED EMBODIMENTS

The process contemplated for preparing the novel compounds of the invention calls for the use of a hindered aldehyde of the structure noted above for reaction with the 8-quinolinol. These aldehydes can be readily prepared through an aldol condensation type reaction wherein two moles of a starting aldehyde react to form a resultant aldehyde condensate. The applicable starting aldehydes can be either branched or normal. The aldol condensation reaction proceeds to the formation of an alpha-beta unsaturated hindered aldehyde which is then hydrogenated to yield the corresponding saturated species. While this technology and that of the hydroformylation route to a variety of the preferred starting aldehydes from terminal olefins is well understood in the art, the overall implementation thereof requires processing equipment representing a huge capital investment. Accordingly; in keeping with the salient objective of the present invention, one is practically constrained to turn to commercial sources of the requisite hindered aldehydes. The foremost source of these aldehydes resides in the commercial production of the "iso-alcohols" marketed extensively for use in the plasticizer and cosmetic fields.

Accordingly, one of such aldehydes is 2-ethylhexanal which is a precursor to iso-octanol. It is marketed in a chemically pure form and at a cost in line with availability of the derivative alcohol as a chemical commodity. Likewise, 2, 4-diethyloctanal is available commercially and marketed as such in good quality at a reasonable cost. Another similarly available hindered aldehyde and one which is representative of the preferred type is a technical grade of hexadecanal prepared by the aldol condensation of n-octanal in turn obtained by the hydroformylation of heptene-1. The foregoing aldehyde is available in the form of the feed stream employed in the OXO process for preparing the alcohol therefrom. Actually, in utilizing hindered aldehydes such as the aforesaid hexadecanal in the practice of the present invention, it is more expedient to start with the alcohol produced therefrom and reduce same to the aldehyde form by a dehydrogenation step. This is so because the alcohol represents the intended commercial end-product and thus there are certain beneficial purification procedures observed in the manufacture thereof which do not lend themselves to the similar treatment of the precursor aldehyde stream. The dehydrogenation procedure applicable in this instance is very simply carried out and involves no special equipment requirements. A representative procedure for accomplishing dehydrogenation will be illustrated in the working examples to follow.

As previously pointed out, the process contemplated for preparing the compounds of this invention can be characterized as an indirect alkylation procedure. In accordance with this procedure the hindered aldehyde reacts with the 8-quinolinol to yield what is believed to be a methalol intermediate which will substantially completely dehydrate in situ to provide the resultant alkylate. The reaction scheme for this procedure is outlined as follows wherein R and R' have the meanings as aforesaid.

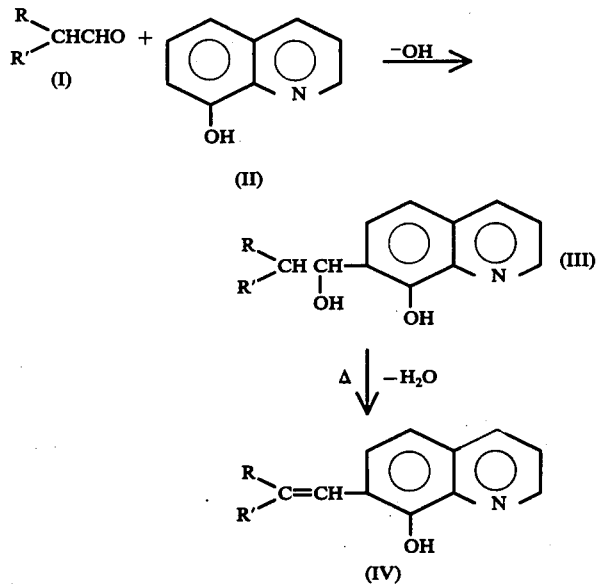

The aldehyde and the quinolinol are preferably reacted in about a stoichiometrical relationship in the presence of a catalytic amount of a strong base such as an alkali metal hydroxide. However, an excess or deficiency of the aldehyde can be observed. The preferred temperature range for reacting the aldehyde and the quinolinol as well as for effecting the dehydration of the resultant methalol intermediate is from about 140° to 200° C. The reaction temperature is not critical but the aforementioned range has been found to provide the optimum results. The reaction can be carried out in the absence of any reaction diluent in which case means are provided for permitting the water to evolve from the reaction mixture. More preferably, however, the reaction is conducted in the presence of a suitable inert solvent capable of facilitating the azeotropic distillation of the evolved water of dehydration. Toluene and xylol represent exemplary solvents for this purpose when operating in the preferred temperature range noted above. Azeotropic distillation is carried out until the evolution of dehydration water essentially completely subsides. Thereafter, the alkylate product can advantageously be recovered by simple distillation means. In the distillation recovery of the alkylate product, it is preferred to observe a pressure not in excess of 5 mm Hg while maintaining a pot temperature in the range of from about 150° to 350° C.

As indicated in the above reaction schematic, the attachment of the hindered aldehyde to the 8-quinolinol occurs predominantly in the number 7 position of the latter. This type substitution is not exclusive, however, as micro hydrogenation and the GLC analysis of the resultant products provide evidence that a very minor degree of substitution occurs in the number 5 position of the 8-quinolinol. There is further evidence from GC analysis that a mixture of geometric isomers are obtained in those instances where R and R' groups of the hindered aldehyde differ.

In order to illustrate to those skilled in the art the best mode contemplated for carrying out the present invention, the following working examples are set forth. As indicated, these examples are given primarily by way of illustration and accordingly, any enumeration of details contained therein should not be interpreted as a limatation on the invention except as such limitations are expressed in the appended claims. All parts and percentages are by weight unless otherwise specified.

EXAMPLE I 7-(2-Ethyl-1-Hexen-1-yl)-8-quinolinol (IV, R=Bu, R'=Et)

Into a suitable reaction vessel equipped with a stirrer, thermometer, reflux condenser and a trap for recovering reaction water were charged 145 parts (1.0 mol) of 8-quinolinol, 100 parts (0.78 mol) of 100% 2-ethylhexanal, 125 parts of toluene, and 1.7 parts of potassium hydroxide. The reaction mixture was refluxed for 21 hours at a liquid temperature of 132° C. During this period of heating, 12.25 parts of water were collected. The reaction mixture was then stripped and the residue product distilled to yield 26.7 parts 8-quinolinol, m.p. 65°–68° C (mixed m.p. 65°–69° C), 33.7 parts of 2-ethylhexanal and 164.6 parts of a yellow oil, b.p. 157°–172° C, $N_D^{20°}$ 1.6186. According to gas chromatography (GC) analysis, the yellow oil product was comprised of 85.1% IV and 12.9% 8-quinolinol. Yield was 79% of IV based on consumed 8-quinolinol. Redistillation yielded a pure fraction of IV of b.p. 179-180° C (5mm), $N_D^{20°}$ 1.6030. Anal. Calculated for $C_{17}H_{21}ON$: C, 80.0; H, 8.33; N, 5.49. Found: C, 79.92; H, 8.37; N, 562.

EXAMPLE II

7(2,4-Diethyl-1-octen-1-yl)-8-quinolinol (IV, R=2-Et hexyl, R'=Et)

Into a reaction vessel equipped as in Example I were charged 122 parts (0.84 mol) of 8-quinolinol, 184 parts of 83.9% active 2,4-diethyloctanal (0.84 mol), 52 parts of toluene, and 3.1 parts potasium hydroxide. The reaction mixture was refluxed for 18 hours at a liquid temperature of 160° C during which period 14.5 parts of water were collected. The reaction mixture was cooled and 3.3 parts of glacial acetic acid were added followed by filtering and stripping to provide 252 parts of a crude product. A portion of this product in the amount of 161 parts was distilled to yield 26.3 parts (GC 78.7% starting aldehyde), b.p. 90°–107° C (15 u) and 66.3 parts of an oily product (GC 81.6%) IV), b.p. 147°–173° C (15 u), and 66.6 part residue which on heating to 355° C yielded an additional 59.4 parts of an oily product (GC 66.1% IV), b.p. 165°–179° C (20 u). Yield: 71% of IV from combined fractions based on consumed 8-quinolinol. Redistillation yielded a pure fraction of IV of b.p. 165°–8° C (30–100 u), $N_D^{20°}$ 1.576. Anal. Calculated for $C_{21}H_{29}ON$: C, 81.0; H, 9.4; N, 4.5. Found: C, 81.13; H, 9.28; N, 4.16.

To a 74 part portion of the original filtered and stripped crude reaction product was added 7.4 parts of activated alumina and a mixture distilled as above to provide two fractions which on combining and redistillation yielded 78% of IV based on consumed 8-quinolinol. The purpose of the foregoing is to illustrate that further dehydration can be accomplished in the distillation step when carried out in the presence of a conventional dehydration catalyst.

EXAMPLE III 7-(1-Hexadecen-1-yl)-8-quinolinol (IV, R and R'=$C_{14}H_{30}$)

A suitable reaction vessel equipped with a stirrer, thermometer and condenser was charged with Enjay Hexadecyl OXO alcohol (technical grade) together with 3% based on the charge of Harshaw 1800P copper chromite catalyst. The alcohol charge was heated and the temperature permitted to rise as needed in order to effect dehydrogenation. The reaction was followed by passing evolved hydrogen through a bubble counter. Heating was continued for a period of 2.25 hours during which time a maximum temperature of 285° C was reached. Conversion to aldehyde was 79.7%.

Into a suitable reaction vessel equipped as in Example I were charged 425 parts of the dehydrogenated alcohol product (1.4 mol as $C_{16}H_{30}O$), 205 parts (1.4 mol) of 8-quinolinol, 109 parts of toluene, and 4.7 parts potasium hydroxide. The reaction mixture was refluxed at a liquid temperature of 164° C for 14 hours until dehydration water ceased to be evolved. The water collected during this period was 20.5 parts. The reaction mixture was cooled and 5.1 parts of glacial acetic acid was added followed by filtering and vacuum stripping at 80° C (10–15 u) to yield 606 parts of a dark crude product which on distillation provided 12.3 parts of crystalline 8-quinolinol, a fraction in the amount of 70.8 parts, b.p. to 115° C (0.55mm which according to GC analysis was approximately 2% 8-quinolinol and a mixture of unreacted aldehydes and lower boiling alcohols. A further fraction in the amount of 66 parts was obtained having a boiling point b.p. 115°–121° C (20u) and which according to GC analysis consisted of 89.5% aldehyde and 6.5% 8-quinolinol. A residue in the amount of 454 parts was obtained. A portion of this residue in the amount of 268 parts yielded 230 parts of an oily product on distillation, b.p. 145°–212° C (0.5 mm) (GC; 74.0% IV and 14.9% 8-quinolinol). The overall yield was 91% of IV based on consumed 8-quinolinol. Redistillation of the foregoing fraction yielded 8-quinolinol, m.p. 69°–71° C, and a major pure fraction of b.p. 229°–239° C (1.2 mm), $N_D^{20°}$ 1.5467. Anal. Calculated for $C_{25}H_{37}ON$: C 81.7; H, 10.2; N, 3.8. Found: C, 81.36, 81.37; H, 10.36, 10.41; N, 3.48, 3.42.

EXAMPLE IV

The purpose of this example is to illustrate the effectiveness of representative compounds of this invention as metal extractants. The illustration will be confined to the static extraction, stripping and phase separation of copper solutions in the presence of a surface active modifier the use of which is conventionally observed in dynamic operations.

EXTRACTION

An organic phase (NAPOLEUM 470) containing 2 vol. % of the alkylate of Example III and 8 vol. % of nonylphenyl as the modifier was contacted for two minutes at room temperature in a separatory funnel with an aqeuous solution containing 1.16 grams per liter (gpl) copper and having a pH of 1.5. Two volumetric organic to aqueous (O/A) phase ratios were observed. The loading capacity of the organic phase in this instance was 1.50 gpl Cu. The results are tabulated as follows:

| O/A | Aqueous Cu cons (gpl) | Organic Cu conc (gpl) | % Cu Extracted |
|---|---|---|---|
| 2 | 0.03 | 0.57 | 97.4 |
| 1 | 0.16 | 1.00 | 86.2 |

An organic phase as above containing 2 vol. % of the alkylate of Example II and 8 vol. % of nonylphenyl was similarly contacted for 1 minute with an aqueous solution containing 1.16 gpl Cu and having a pH of 1.5. The organic loading capacity was 1.72 gpl Cu. The results are tabulated as follows:

| O/A | Aqueous Cu cons (gpl) | Organic Cu conc (gpl) | % Cu Extracted |
|---|---|---|---|
| 2 | 0.07 | 0.55 | 94.0 |
| 1 | 0.15 | 1.01 | 87.1 |

STRIPPING

An organic phase containing 2 vol. % of the alkylate of Example II and 8 vol. % nonylphenyl was loaded to contain 0.97 gpl Cu. The loaded organic phase was then contacted with a like volume of an aqueous stripping solution containing 25 gpl Cu and 150 gpl conc. $H_2SO_4$. After 2 minutes of contact the phases were allowed to separate whereupon it was determined that the copper content of the organic phase was 0.09 gpl indicating that over 90% of the copper was stripped.

An organic phase containing 2 vol. % of the alkylate of Example III and otherwise similar to that above was loaded to contain approximately 1 gpl Cu. The loaded organic phase was contacted with a like volumetric amount of an aqueous stripping solution containing 128.7 gpl conc. $H_2SO_4$ and 24.8 gpl Cu. After stripping contact for 2 minutes, the copper content of the organic phase was reduced to 0.05 gpl.

PHASE SEPARATION

Extraction phase separation was conducted by contacting 500 ml of a 2 vol. % of the alkylate of Example III and a 8 vol. % nonylphenyl in NAPOLEUM 470 with 500ml of a 1 gpl copper aqueous solution having a pH of 1.8 in a 1 liter graduated cylinder. The two phases were dispersed at room temperature for 2 minutes with the aid of a mechanical stirrer. Complete phase separation occurred in 2 hrs. 50 mins. after mixing was terminated.

For stripping phase separation, the above organic phase was contacted for 2 minutes with an aqueous stripping solution consisting of 128.7 gpl conc. $H_2SO_4$ and 24.8 gpl Cu in the same manner as above. Complete phase separation occurred in 3 minutes.

Extraction phase separation of the alkylate of Example II was run under the same conditions as above. Phase separation time was 2 hrs. 15 mins. Stripping phase separation was also run in the same manner with the exception that the stripping solution contained 150 gpl conc. H₂SO₄ and 25 gpl Cu. Phase separation time was 5 hrs. 50 mins.

I claim:

1. A process for preparing a compound of the formula:

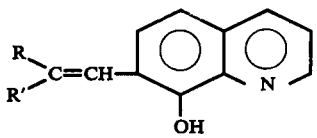

wherein R and R' represent alkyl groups having a sum total of 6–18 carbon atoms, which comprises the steps of heating at a temperature of about 140°–200° C. substantially equal molar amounts of 8-hydroxyquinoline and a hindered aldehyde of the formula:

wherein R and R' have the above-mentioned meanings, to effect the condensation thereof and the concomitant removal of water of dehydration from the condensate and thereupon distilling the reaction product to recover the resultant alkylate.

2. A process in accordance with claim 1 wherein the removal of the water of dehydration is effected by azeotropic distillation.

3. A process in accordance with claim 2 wherein the solvent is toluene, xylene or a mixture thereof.

4. A process in accordance with claim 3 wherein said distillation step is carried out on a reaction product freed of solvent at a pressure not in excess of 5mm Hg at a pot temperature of from about 150° to 350° C.

* * * * *